(12) United States Patent
Lasch et al.

(10) Patent No.: US 9,171,709 B2
(45) Date of Patent: *Oct. 27, 2015

(54) ANALYSIS OF MICROBES BY MALDI MASS SPECTROMETRY

(71) Applicant: Bruker Daltonik GmbH, Bremen (DE)

(72) Inventors: Peter Lasch, Berlin (DE); Dieter Naumann, Berlin (DE); Maren Stämmler, Petershagen (DE); Thomas Maier, Lilienthal (DE); Jens Boβmeyer, Bremen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/405,642

(22) PCT Filed: Jun. 6, 2013

(86) PCT No.: PCT/EP2013/061722
§ 371 (c)(1),
(2) Date: Dec. 4, 2014

(87) PCT Pub. No.: WO2013/182648
PCT Pub. Date: Dec. 12, 2013

(65) Prior Publication Data
US 2015/0136972 A1    May 21, 2015

(30) Foreign Application Priority Data
Jun. 8, 2012    (DE) .......................... 10 2012 011 647

(51) Int. Cl.
*H01J 49/04*    (2006.01)
*H01J 49/26*    (2006.01)
(Continued)

(52) U.S. Cl.
CPC ............ *H01J 49/164* (2013.01); *G01N 33/569* (2013.01); *H01J 49/0027* (2013.01)

(58) Field of Classification Search
CPC ... C12Q 1/04; G01N 33/6848; G01N 33/569; H01J 49/0418
USPC ............... 250/288, 282, 281; 435/405, 173.7, 435/40.5
See application file for complete search history.

(56) References Cited

U.S. PATENT DOCUMENTS 4,617,265 A    10/1986 Peterson
5,808,300 A *  9/1998 Caprioli ........................ 250/288
(Continued)

FOREIGN PATENT DOCUMENTS

DE    102004020885 A1    11/2005
DE      60317314 A1    9/2008
(Continued)

OTHER PUBLICATIONS

Bruker Daltonik GmbH, "Instructions for Use MALDI Biotarget 48. Disposable MALDI Targets for Microorganism Identification," www.care-bdal.de, Dec. 2011.
(Continued)

*Primary Examiner* — Nikita Wells
(74) *Attorney, Agent, or Firm* — Robic, LLP

(57) ABSTRACT

The invention relates to methods for the mass spectrometric analysis of microbes, in particular to a transfer method of microbes that are required to be identified from agar plates onto mass spectrometric sample supports and their preparation for ionization by matrix-assisted laser desorption (MALDI). Microbes from microcolonies which have grown on the agar plates after a culture time of only six to eight hours are transferred with a high transfer yield onto contact surfaces of suitable size by direct contact and cell disrupted on the contact surface; the released proteins are prepared with matrix material on the contact surface as MALDI samples. The ionization by matrix-assisted laser desorption also takes place on the contact surface.

16 Claims, 4 Drawing Sheets

(51) Int. Cl.
*B01D 59/44* (2006.01)
*G01N 30/72* (2006.01)
*H01J 49/16* (2006.01)
*G01N 33/569* (2006.01)
*H01J 49/00* (2006.01)

(56) References Cited

U.S. PATENT DOCUMENTS

| | | |
|---|---|---|
| 7,166,441 B2 * | 1/2007 | Nadler et al. .................. 435/23 |
| 8,835,176 B2 * | 9/2014 | Bossmeyer et al. ........... 435/405 |
| 2003/0175844 A1 | 9/2003 | Nadler et al. |
| 2007/0065946 A1 | 3/2007 | Reboud et al. |
| 2007/0275478 A1 | 11/2007 | Taranenko et al. |
| 2010/0248298 A1 | 9/2010 | Kostrzewa et al. |
| 2014/0227723 A1 * | 8/2014 | Ingber et al. ................. 435/7.92 |

FOREIGN PATENT DOCUMENTS

| | | |
|---|---|---|
| DE | 102009007266 A1 | 10/2010 |
| DE | 102010019869 A1 | 11/2011 |
| DE | 102010033105 A1 | 2/2012 |
| EP | 2354796 A1 | 8/2011 |
| WO | 03044825 A1 | 5/2003 |
| WO | 2012016929 A1 | 2/2012 |
| WO | WO2013182648 A1 | 12/2013 |

OTHER PUBLICATIONS

Lange, Oliver, "MIROB: Automatic rapid identification of microorganisms in high through-put" Industrial Robot: An international Journal, 35/4 (2008), Oct. 11, 2008, p. 311-315.

Maquelin, K. et al., Raman spectroscopic method for identification of clinically relevant microorganisms growing on solid culture medium, Analytical Chemistry, Jan. 1, 2000, vol. 72, pp. 12-19.

* cited by examiner

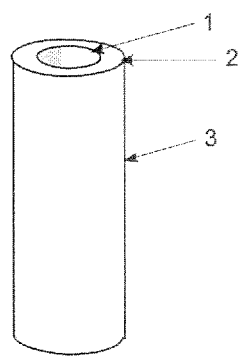
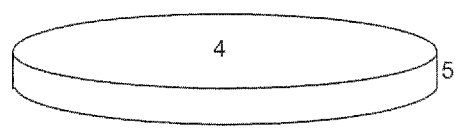
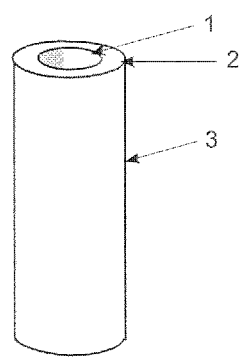
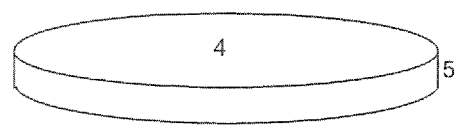
Figure 1                                  Figure 2
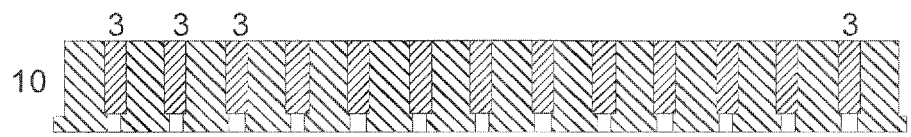
Figure 3
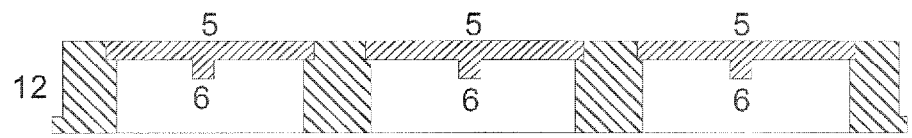
Figure 4

ANALYSIS OF MICROBES BY MALDI MASS SPECTROMETRY

FIELD OF APPLICATION

The invention relates to methods for the mass spectrometric analysis of microbes from colonies on surfaces of nutrient media, particularly in a mass spectrometer with ionization by matrix-assisted laser desorption (MALDI).

PRIOR ART

The routine, fast and error-free analysis of microorganisms plays an important role particularly in clinical and extra-clinical infection diagnostics, in hygiene monitoring in hospitals or in rivers and lakes used for swimming, in food analysis, in monitoring and control of biotechnological processes and in microbiological research. The term microorganisms, here called microbes for short, describes all microscopically small organisms, for example unicellular fungi (e.g. yeasts), algae, or protozoa (e.g. plasmodia as malaria pathogens), although the focus of the identification work is usually on bacteria.

The identification of microbes means, in principle, determining their species and thus categorizing the microbes into the taxonomic hierarchy: domain (bacteria, archaea and eukaryotes), kingdom, phylum, class, order, family, genus, and species. In addition to a taxonomic identification, the analysis of microbes can also comprise their characterization in terms of other properties, such as the pathogenicity of a microorganism (ability to cause disease) or the resistance of a microorganism against antibiotics. In this document, the identification is in particular directed to the identification on the species level.

For mass spectrometric identification methods, microbes of samples taken for analysis are usually cultured on nutrient media in Petri dishes to form colonies. The time between the samples for analysis being delivered to the analytical laboratory and the identification of the species is essentially dictated by the time needed for culturing, because the actual mass spectrometric determination takes only minutes. At present, this culture often takes between 18 and 24 hours. This is too long for many applications, particularly for applications in medical diagnostics. There is therefore an urgent need to significantly shorten the time required for the mass spectrometric identification, particularly to one working day.

With the methods currently used, the nutrient medium for the culture is usually in an agar in a Petri dish (agar plates); this enables pure "isolates" in separate colonies to be cultured. Agar is a gelatinous galactose polymer comprising by far more than 90 percent water. The agar itself is indigestible and is attacked hardly at all by microbes. Since the microbes are mainly sampled manually at present, the colonies should have diameters of at least half a millimeter, better at least one millimeter, for reliable sampling of the microbes. To culture colonies of this size takes many hours, or sometimes even days, depending on the vigor of the microbes. For clinically important species, the samples on agar plates are usually cultured for around 18 to 24 hours nowadays. If the colonies overlap or mix, isolated colonies are obtained in a second culture.

During the manual preparation of a MALDI sample, a small quantity of a selected colony is transferred from the surface of the nutrient medium onto a sample support; in practice this is often done with a wooden tooth pick which is disposed of afterwards. The transferred microbes are then sprinkled with a strongly acidified solution of a conventional matrix substance (usually α-cyano-4-hydroxy cinnamic acid, HCCA, or 2,5 di-hydroxy-benzoic acid, DHB) for a subsequent ionization by matrix-assisted laser desorption (MALDI). The acid (usually formic acid or trifluoroacetic acid) attacks the cell walls, which means that the organic solvent (usually acetonitrile) of the matrix solution can penetrate into the microbial cells and cause their weakened cell walls to burst by osmotic pressure. The destruction of the usually resilient cell walls is called "cell disruption"; cell disruption releases the soluble proteins from the cell. The sample is then dried by evaporating the solvent, causing the dissolved matrix material to crystallize. The released soluble proteins of the microbes, and also other substances of the cell to a small extent, are incorporated into the matrix crystals during crystallization. This process produces a sample preparation on the sample support, which is called a "MALDI sample" below.

The MALDI samples with the embedded analyte molecules are bombarded with focused UV-laser pulses of a few nanoseconds duration in a mass spectrometer, thus generating ions of the analyte molecules in the vaporization plasmas. These ions can then be separated from each other in the mass spectrometer according to the mass of the ions, and can be measured. Currently, simple time-of-flight mass spectrometers without a reflector are used for the mass spectrometric identification of microbes in order to achieve the highest sensitivity.

The mass spectrum obtained is the profile of the mass values of the analyte ions from the microbes. The ions here are predominantly protein ions, and the ions with most useful information for the identification have masses of between approximately 3,000 daltons and 15,000 daltons. In this method the protein ions are very predominantly only singly charged (charge number $z=1$), which is why one can also simply talk about the mass m of the ions here, instead of always using the term "mass-to-charge ratio" $m/z$, as is actually necessary in mass spectrometry. The identification is carried out by similarity comparisons between the mass spectra acquired from the microbes, i.e. microbial cells of the sample for analysis, and reference spectra from a reference library; see the document DE 10 2010 006 450 A1 (M. Kostrzewa), which also contains a detailed description of the mass spectrometric method. For medical applications, suitable reference libraries with reference mass spectra from several thousand microbe strains are now commercially available, validated according to the regulations of many countries.

The mass spectrometric method for the identification is very robust; changes to the culture conditions or the preparation methods have hardly any effect on the identification results because practically only genetically defined proteins with genetically defined abundances are analyzed for each species. Around 60 to 85 percent of the proteins originate from the ribosomes, which comprise a fixed number of between 40 and 60 different protein molecules, depending on the species. Each bacterial cell contains several ten thousand identical ribosomes; cells of eukaryotes contain several hundred thousand. The abundances of the measured protein molecules therefore do not depend on the nutritional conditions or the maturity of the colony, as is the case with lipoproteins or fatty acids serving as energy stores, for example; the abundances of the ribosomal protein molecules is essentially equal for all proteins and equal to the number of ribosomes. The robustness of the method makes it possible to use microbes from very young, or mature or even ageing colonies for the identification, and approximately the same identification results are achieved.

To date the, there is a rule of thumb saying that around $10^5$ microbes at least are required for preparing a MALDI sample on the sample plate in order to guarantee reliable mass spectrometric identification of the microbes. This quantity is hardly discernible with the naked eye. Quantities between $10^5$ and $10^7$ are particularly suitable. In the case of eukaryote cells with several hundred thousand ribosomes, mass spectra usable for identification of the species have been successfully obtained from individual cells. But for bacteria, whose hard cell walls require special cell disruption processes, it has so far only been possible in isolated cases to produce mass spectra which are good enough for identification from only $10^3$ bacteria or less.

The mass spectrometric method of identification has proven to be extremely successful. It is very fast once culturing has been completed, and the certainty of correct identification is far greater than with the microbiological identification methods currently in use, as has been demonstrated in various studies.

The mass spectrometric method allows microbes to be identified from a pure culture of microbes, a so-called "isolate". The mass spectrum of a pure culture does not contain any superimposition of signals from other microbes. It has, however, been found that mass spectra of mixtures of two microbial species can also be evaluated, if need be, and that both species of microbe can be identified (see the document DE 10 2009 007 266 A1, M. Kostrzewa et al., for example). The identification certainty suffers only slightly.

The pursuit of automation has led to devices which replace manual transfer with machine transfer using a small inoculating rod. The Fraunhofer Institute for Factory Operation and Automation (Magdeburg/Germany) has developed a robot called "MiRob", which can perform this task (cf.: O. Lange et el. (2008) "MIROB: automatic rapid identification of microorganisms in high throughput", Industrial Robot: An International Journal, Vol. 35 Iss: 4, pp. 311-315 or patent DE 10 2004 020 885 B2). The robot is manufactured as MiRob 300i by the company Mess-, Prüf- and Handling-Systeme GmbH, Reutlingen/Germany. As is the case with manual transfer, the microbes are transferred indirectly onto the mass spectrometric sample support by means of a tool, in this case an inoculating rod. Here too, the colonies should have a minimum diameter of 0.5 millimeters. The transfer tools used to date (tooth picks, inoculating rods) are designed to be used only once. A direct transfer of the microbes onto an analytically used sample support for the acquisition of infrared spectra of the microbes by infrared microscopy is known from the document EP 0 456 995 B1 (D. Naumann and H. Labischinski, 1989, corresponding to U.S. Pat. No. 5,660,998).

OBJECTIVE OF THE INVENTION

The objective of the invention is to define methods for the mass spectrometric analysis of microbes with which the time required from the delivery of samples to be investigated (sample for analysis) through to the identification is significantly shortened in comparison with current methods, preferably to one working day, i.e. to about eight hours. The method should also be reliable and capable of automation, and should require little consumable material.

SUMMARY OF THE INVENTION

The present invention provides a method for the mass spectrometric analysis of microbes on the surface of a nutrient medium in a mass spectrometer, comprising the steps: (a) microbes are transferred by direct contact of the surface of a sample support with the surface of a nutrient medium, (b) the transferred microbes are disrupted on the surface of the sample support, and the molecular constituents of the microbes are prepared for mass spectrum acquisition on the surface of the sample support, and (c) the sample support with the prepared samples on the surfaces is transferred to the mass spectrometer for analysis to acquire a mass spectrum of the molecular constituents for their identification by comparison with reference mass spectra.

The present invention provides a method for the mass spectrometric analysis of microbes on the surface of a nutrient medium in a mass spectrometer, comprising the steps: (a) microbes are transferred onto a contact surface of a sample support by direct contact, (b) the transferred microbes are cell disrupted on the contact surface of the sample support, and (c) the sample support with the molecular constituents of the disrupted microbes are introduced into the mass spectrometer for analysis.

The present invention provides a method for the mass spectrometric analysis of microbes on the surface of a nutrient medium in a mass spectrometer with ionization by matrix-assisted laser desorption, comprising the steps: (a) microbes are transferred by direct contact onto a contact surface of a sample support, (b) the transferred microbes are cell disrupted on the contact surface of the sample support, and the molecular constituents of the disrupted microbes are prepared as a MALDI sample, and (c) the sample support with the MALDI sample is transferred to the mass spectrometer for analysis. The cell disruption of the microbes is preferably carried out by the preparation of the MALDI sample, for example by the addition of a suitably aggressive matrix solution (matrix substance in a strongly acidified organic solvent).

Other types of ionization where the substances to be ionized are located on a sample support can also be used instead of MALDI ionization, such as cluster ionization in accordance with EP 1 200 984 B1, Desorption Electrospray Ionization (DESI) in accordance with WO 2005/094389 A2 or Matrix Assisted Laser Desorption Electrospray Ionization (MALDESI) in accordance with DE 10 2004 002 729 A1. Here, the preparation of a mass spectrometric sample can consist in the cell disruption of the microbes on the sample support. In the following, however, the description mainly is based on MALDI as the ionizing process.

The method according to the invention is suitable for the identification of most clinically relevant microbes with a culture period of around eight hours at maximum and thus within one working day or during a short night. During this short time, usually only microcolonies with an approximate diameter of 50 to 200 micrometers are formed on the surfaces of nutrient media. Even for slow-growing microbes, which until now have had to be cultured for many days, the time can be reduced to half or even less.

Microbes from microcolonies that have formed after only six to eight hours of culture for many diagnostically relevant microbes, are transferred directly onto the sample support with a high transfer yield by bringing surfaces of the sample supports into direct contact, even if the microbes exist only in the form of microcolonies. The microbes are disrupted on these contact surfaces, and the proteins released are prepared with matrix materials on the contact surface of the sample supports to become MALDI samples. The ionization by matrix-assisted laser desorption also takes place on the contact surfaces of the sample support. Surprisingly, sufficiently good mass spectra can be obtained from microcolonies having only around 1000 microbes. The reasons for this high sensitivity are not known in detail: it is possible that, unlike manual transfer onto a sample support, the direct contact transfers only clean microbes without any agar material attached and with only little nutrient medium solution. In addition, there are no losses due to microbe material adhering to the transfer tool and remaining there instead of being transferred onto a sample support. The method according to the invention also allows the use of sample supports with high adhesiveness for microbes; this is unsuitable for a transfer tool because it also has to release the microbe material again. For most of the clinically relevant microbes, the critical period from delivery of the samples for analysis through to identification of the microbes can be reduced from around 18 to 24 hours to only around eight hours.

The invention thus essentially consists in transferring the microbes of a colony, in particular a microcolony, located on the surface of the nutrient medium, usually an agar plate, onto a suitably shaped contact surface of a suitable sample support by direct contact, without using special transfer tools, such as the tooth picks mentioned above. A far higher percentage of the microbes from a microcolony can be transferred onto a sample support by this direct contact transfer than is possible with a tool. The microbes are then directly cell disrupted on the contact surface and prepared as a MALDI sample; the sample support with the contact surface is then introduced into the ion source of the mass spectrometer, having first been inserted into a suitable adapter plate, if necessary. The MALDI ionization therefore takes place directly on the contact surface of the sample support.

The microbes can be transferred directly onto a pin-shaped sample support (sample support pin), whose end surface is brought into contact with microbes. The contact surface of the pin-shaped sample support is so small that only microbes of one individual colony are transferred onto the pin-shaped, sample support. After the microbes have been transferred, the pin-shaped sample support is preferably inserted into an adapter plate in such a way that the end surface of the pin-shaped sample support is essentially flush with the surface of the adapter plate. "Essentially flush" means here that a mass spectrometric analysis in a MALDI time-of-flight mass spectrometer with axial ion injection is possible with sufficient mass resolution. Microbes from different colonies can be transferred onto separate pin-shaped sample supports, which are inserted together into an adapter plate and introduced into the mass spectrometer in the adapter plate. It is also possible to transfer microbes from one colony onto several pin-shaped sample supports.

A method according to the invention using pin-shaped sample supports comprises the following steps: acquiring an image of the surface of the nutrient medium, determining the positions of colonies from the image, performing contact transfer of microbes at the determined positions onto separate pin-shaped sample supports, inserting the pin-shaped sample supports into an adapter plate, preparing MALDI samples from the microbes on the pin-shaped sample supports, introduce the adapter plate into a mass spectrometer, and acquiring spectra with ionization by matrix-assisted laser desorption at the positions of the pin-shaped sample supports in the adapter plate.

The microbes can also be transferred directly onto a plate-shaped sample support (sample support plate), whose contact surface is so large that microbes from several colonies are simultaneously transferred onto the plate-shaped sample support. After the transfer, one or more plate-shaped sample supports can be arranged on an adapter plate and fastened there, by mechanical or magnetic forces, for example. The diameter of the plate-shaped sample support is preferably between one and eight centimeters.

The contact surface of the plate-shaped sample support can be imaged after the microbes have been transferred, e.g. with a digital camera, in order to determine the positions of the transferred microbes on the plate-shaped sample support from the image taken. This is preferably done after the plate-shaped sample support has been arranged on an adapter plate, and comprises the recording of markings of the adapter plate, from which the position of the sample support, or positions of the transferred microbes, relative to the adapter plate are determined. This allows a directed positioning of the transferred microbes in the ionization region of the MALDI source. Equally, the surface of the nutrient medium can be imaged and the position of the plate-shaped sample support relative to the surface of the nutrient medium can be determined in order to identify the positions of the transferred microbes on the plate-shaped sample support. The matrix solution is then preferably applied to the whole contact surface of the plate-shaped sample support, but the mass spectrometric analyses are only carried out at the determined positions. On the other hand, the MALDI samples can be prepared only at the determined positions and the mass spectrometric analyses carried out only there. The contact surface of the plate-shaped sample support and the surface of the nutrient medium are preferably imaged with the aid of light-optical measurement procedures, most preferably with a reflected-light microscope in the visible spectral range. The light-optical measurement procedure can also be a spatially resolved measurement of scattered light, Raman scattering or fluorescence. The imaging of the contact surface of the plate-shaped sample support is preferably done before the microbes are cell disrupted, but can also be done after the cell disruption of the microbes.

A sample under investigation is usually spread (plated, inoculated) onto the surface of a nutrient medium in the form of a diluted solution, which initially creates spatially separated microcolonies. When plate-shaped sample supports are used, the microbes of the microcolonies are transferred onto spatially separate areas of the sample support, which means they can be mass spectrometrically identified without mutual influence (mixing), which is advantageous particularly when different species of microbe are present in the sample to be investigated (mixed sample). The sample for analysis can also be applied to the surface of the nutrient medium in the form of a track, which limits the growth of the microbes, and thus the positions of the microcolonies, to the track. The track can already be recorded when the sample for analysis is being applied to the surface of the nutrient medium (inoculation process). After the microbes have been cultured, a plate-shaped sample support is brought into contact with the surface of the nutrient medium, and the position of the plate-shaped sample support in relation to the surface of the nutrient medium is determined, from which the track on the contact surface of the sample support is determined. A matrix solution is then applied to the whole contact surface of the plate-shaped sample support and the mass spectrometric analyses are carried out only along the determined track. Following the track without having first imaged the surface of the nutrient medium or the contact surface makes it possible to also identify microbes in microcolonies which are not yet discernible in the corresponding images, without having to mass spectrometrically analyze the whole sample support. It is also possible to prepare MALDI samples only along the determined track.

The contact surface of the sample supports can, for example, be the surface of a flat sample support plate with any outer contour, measuring around one to eight centimeters in diameter. Such a support plate can simultaneously pick up the microbes of many colonies by being gently placed or pressed onto the surface of the nutrient medium while being aligned parallel to the surface. The contact surface, however, can also be simply the end surface of a sample support pin measuring only around two millimeters in diameter for the removal of microbes from only one selected colony, particularly a microcolony.

The contact surface of the sample supports can be coated in a particular way in order to transfer as many microbes as possible. It can simply be moistened, for example, or prepared with protein-adsorbing or adhesive areas which have a high affinity for microbes and are thus able to hold onto them. For example, a thin layer preparation with α-cyano-4-hydroxycinnamic acid (HCCA) generates a microcrystalline surface which finally adsorbs peptides or proteins and thus also the coat proteins of bacteria. A moistened, thin layer of dinitrocellulose or trinitrocellulose also adsorbs proteins and at the same time has a positive effect on the MALDI process.

A digital image can be obtained of the surface of the nutrient media before the microbes are removed in order to determine information on the position of the microcolonies. The information can be used to control the removal of microbes from the nutrient media, in particular removal with thin sample support pins. A digital image of the transferred microbes on plate-shaped sample support plates gives the positions of the microbes on their contact surfaces; this information can be used to control the scanning of larger sample support plates with the laser beam during the spectrum acquisition.

Additionally, one has to ensure that the preparation of the microbes on the contact surface is directed toward maximum ion yield by special measures such as demineralization and uniform embedding of the microbe proteins in thin matrix layers.

The methods according to the invention have the advantage over the Prior Art that they require less consumable material because transfer tools are not required, and they cause therefore lower costs, and that they save time for the cultivation of the microbes, resulting in faster identification. Compared to the manual transfer of microbes from different samples for analysis onto a mass spectrometric sample support, transfer via direct contact makes it possible to avoid mistakes in the sample assignation, by automatically transferring an identification label of each sample for analysis to each mass spectrometric sample support used. This identification label is stored on the support of the nutrient medium.

BRIEF DESCRIPTION OF THE ILLUSTRATIONS

FIG. 1 depicts an example for a simple sample support pin (3), with an end surface acting as the contact surface, which is coated in the center (1) with a protein-adsorptive layer with a hydrophobic border (2). The sample support pin (3) has a diameter of around 2 millimeters in this example and is around eight millimeters long.

FIG. 2 shows a sample support plate (5) with contact surface (4). The sample support plate (5) is round in this example, but can also have any other outer contours with an area measuring between one and eight centimeters in diameter. The area of the sample support plate preferably corresponds to the area of the nutrient medium, i.e. approximately the shape and area of a Petri dish.

FIG. 3 shows how the sample support pins (3) are inserted into an adapter plate (10) in such a way that their end surfaces are flush with the surface of the adapter plate.

FIG. 4 shows an adapter plate (12) with sample support plates (5) which are inserted so as to be flush. The sample support plates (5) have handles (6) on the rear with which they can be gripped by a robotic system and pressed onto the plates of nutrient medium.

Figure 5:
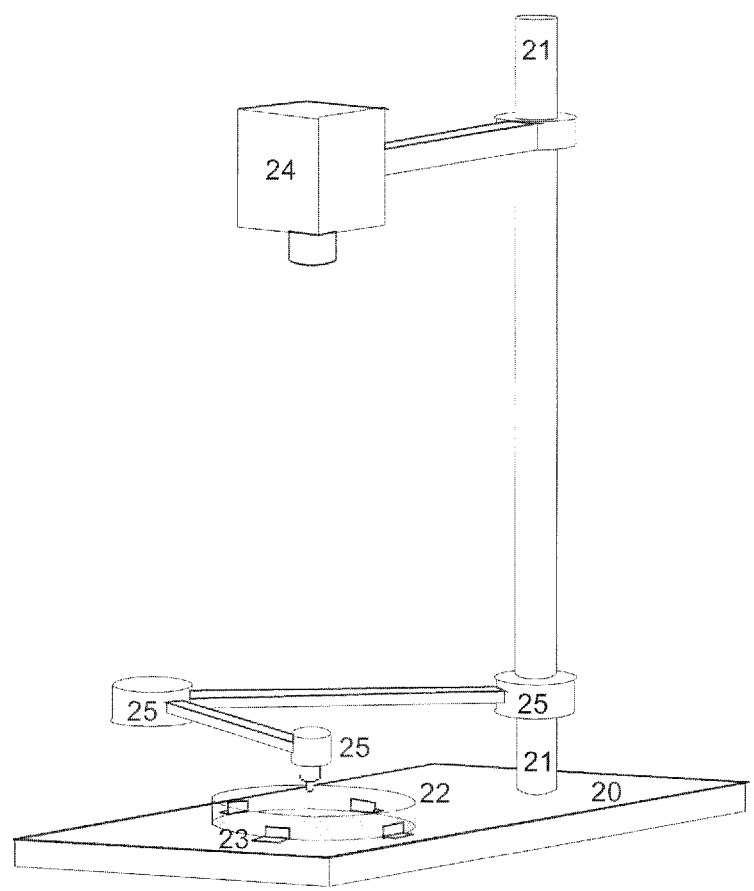

FIG. 5 shows an arrangement for the contact transfer of microbes, with base (20) and support column (21). A Petri dish (22) is fixed on the base (20) with clamps (23). A camera (24) mounted on the support column (21) can take digital images of the surface of the nutrient medium in the Petri dish (22). A robotic arm (25) with controllable joints can press sample support pins (3) and also sample support plates (5) onto the nutrient medium in the Petri dish (22) with high positional accuracy.

Figure 6:
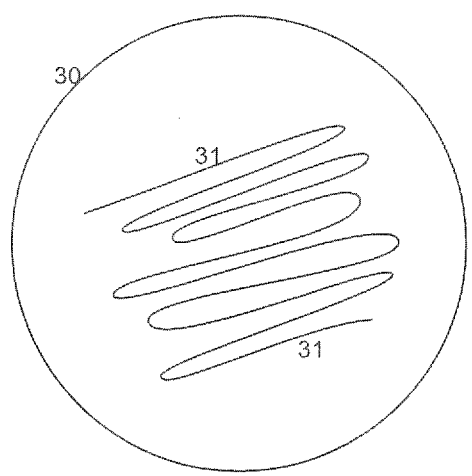

FIG. 6 depicts a Petri dish (30) in plan view, with a track (31) of a manually applied sample for analysis (analyte solution). The inoculation process can be digitally photographed, and after the microbe colonies have been removed by contact transfer, the image (or video recording) can serve to control the laser scanning on the contact surface of the sample support plate during the mass spectrometric analysis.

Figure 7:
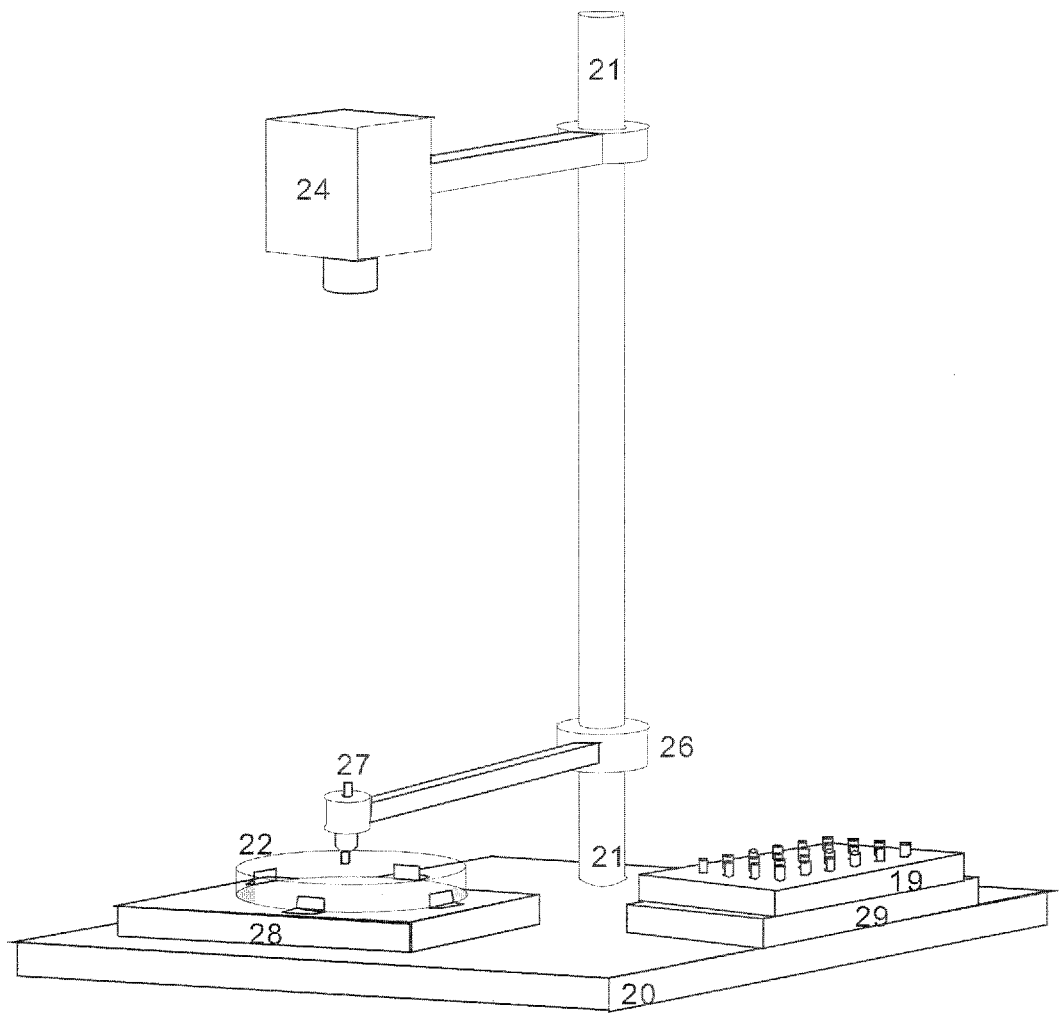

FIG. 7 represents a slightly different version of the device for transferring the microbes compared to the one shown in FIG. 5. The robotic arm is replaced here by a rigid arm which can only be rotated between two fixed angular positions by the joint (26). The rigid arm has a device (27) which can hold a sample support pin and lower it onto the surface of the nutrient medium in the Petri dish (22). The correct contact position is generated by a movement device (28) for the Petri dish (22) which can operate horizontally in two directions. After the device (27) is rotated about the joint (26), it can take a sample support pin from the storage container (19) or replace it again, the storage container (19) being moved to the correct position by the movement device (29).

Figure 8:
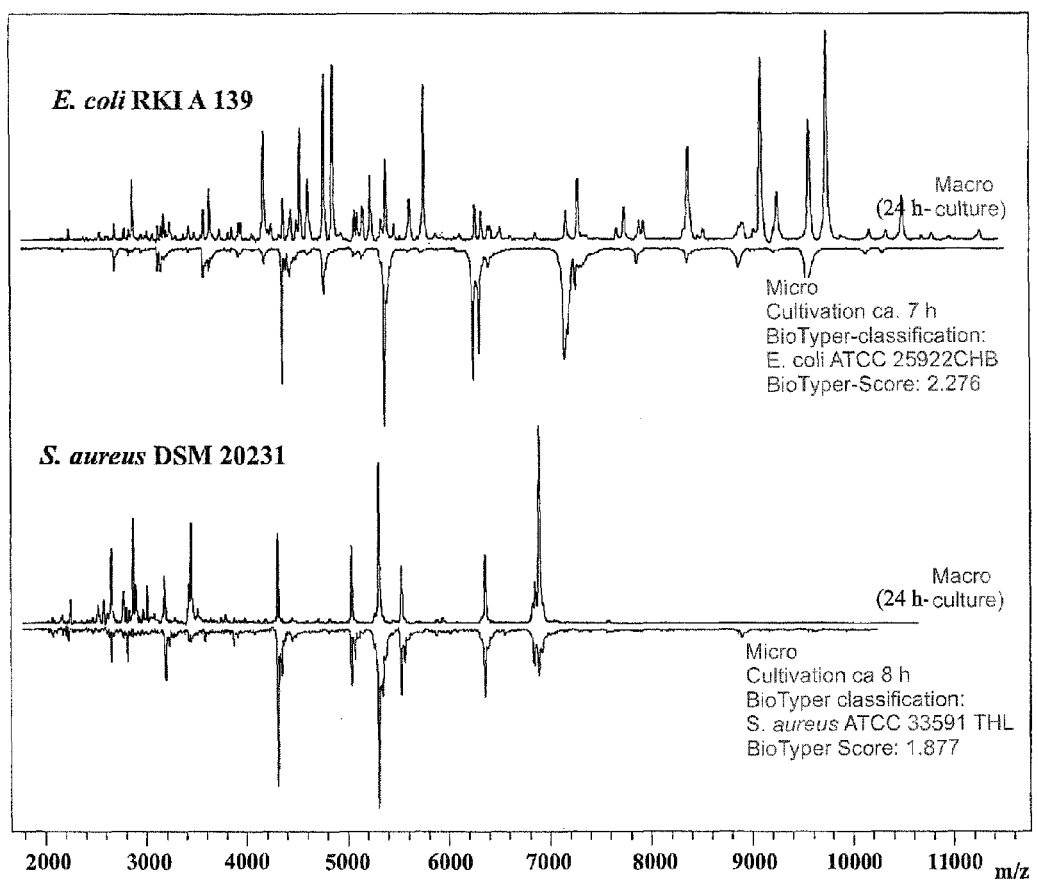

FIG. 8 shows a comparison of mass spectra of different sample transfer techniques for MALDI-TOF mass spectrometry using two test microorganisms (*E. coli* RKI A139 and *S. aureus* DSM 20231). The spectra pointing upwards ("Macro") were recorded using samples prepared with the current technique from 24-hour cultures. For the spectra pointing downwards ("Micro"), contact transfer for microcolonies was used. Although marked differences can be seen between the respective micro- and macro-spectra, the BioTyper™ database comparison of micro-spectra with stored reference spectra from 24-hour cultures resulted in a correct species identification with good (*S. aureus*) or very good (*E. coli*) score values.

PREFERRED EMBODIMENTS

Growth of microbes takes place in four phases. In an initial, short adjustment phase ("lag phase") the metabolism of the microbe adjusts to the nutrient medium, by producing different digestion enzymes, for example. This is followed by a phase of unhindered growth with exponential increase of the microbes ("log phase") until a shortage of nutrients or the production of toxins stops the exponential increase and asymptotically leads into a "stationary phase". Finally, the microbes die due to a lack of nutrients or poisoning ("death phase"). During the phase of unhindered growth, divisions of the bacterial cell take place after characteristic periods of time each, the "generation time". The generation times depend on the species of microbe and the external conditions; for optimum conditions (temperature, nutrient medium) the times for one generation in each case are between 15 minutes and 24 hours. Most of the clinically important pathogenic microbes divide after relatively short periods of time between 15 and 45 minutes; but there are also clinically important exceptions with slow growth.

These growth phases refer to the growth in liquid nutrient media, however. The growth on agar plates is necessarily different because the unhindered exponential growth can only take place for a short time in a colony on the surface. Unhindered growth occurs only at the edge of the colony. Within the area of the colony, microbes are pushed upward by divisions into a second, third and fourth layer, which decreases the supply of nutrients. Some microbes are locked into these top layers, but some can move across the lowest microbe layer toward the edge, where they again obtain access to nutrient media. In the case of virulent microbes, after eight hours microcolonies have been grown comprising between $10^3$ and $10^5$ cells, for slow-growing microbes, the microcolonies comprise even fewer cells.

For the embodiments described below, the microbes, in particular bacteria, from a sample for analysis are plated in the usual way onto a plate containing a nutrient medium, an agar plate, for example, and cultured in an incubator for six to eight hours at optimum temperature (usually 37° Celsius). The microcolonies described above then grow on the surface of the nutrient medium. The nutrient medium is preferably in a Petri dish. The surface of the nutrient medium should be such that microbes can easily be lifted from it, i.e. the microbes should not penetrate through the surface into the nutrient medium.

FIG. 5 depicts a device which can be used to remove the microbes from the microcolonies by contact transfer. The Petri dish (22) is fixed on the base (20) of the device with small clamps (23). Before the microbes are removed, it is expedient to take a digital image of the surface of the nutrient medium with a camera (24) in order to determine the positions of the microcolonies. The camera is preferably digital cameras and should be adapted to the task; in most cases, a macroscopic optics is suited well taking a single picture, but sometimes the surface has to be precisely scanned with a microscope lens system. The positional data of the microcolonies can be determined automatically with the aid of image recognition methods. It is also possible to determine the microcolonies visually by clicking on their position on a screen displaying the image, and thus select them for a transfer. Microcolonies with only 1000 bacteria have an approximate diameter of 0.05 millimeters; even these can still be photographically identified if the lighting is correct. In the favorable case, microcolonies of diagnostically important bacteria contain a few thousand to a few ten thousand bacteria after eight hours of incubation time.

If the automatic image recognition method is used to determine the positions of the microcolonies, it is then possible to also automate the selection of the microcolonies for identification by specifying parameters for a characterization of the microcolonies, such as the shape of the colony. The parameters can particularly relate to the size, shape, reflection intensity and color of the microcolonies.

In a first embodiment, small sample support pins (3), as shown in FIG. 1, are each pressed with their end surface, which measures a maximum of around nine, preferably less than four square millimeters, centrally onto a selected microcolony in order to transfer microbes from the microcolony by contact onto the end surface of the sample support pin (3). A sample support pin (3) measuring two millimeters in diameter is shown in FIG. 1. The sample support pins (3) should consist of electrically conductive material, for example metal or conductive plastic. They can be pressed onto the microcolony manually, but it is better to use the robotic arm (25) of the device from FIG. 5, which is controlled by the positional data from the optical image of the surface of the nutrient medium. Even more advantageous is a device according to FIG. 7, which also allows the sample support pins to be removed from and put back into a storage container (19). The sample support pins (3) can then be inserted precisely flushing into corresponding holes in suitable adapter plates (10), which are suitable for being introduced into the mass spectrometer. When a storage container (19) is used, it is easy to transfer all the sample support pins together into the adapter plate by simply placing the adapter plate with the insertion holes pointing downwards onto the filled storage container, turning both containers over, and removing the storage container again. The end surfaces of the sample support pins (3) can be roughened or smooth; the end surfaces can also be prepared in a special way, as is shown in FIG. 1, to enable them to keep hold of as many microbes as possible. The sample support pins (3) are usually designed for single use, as is advantageous for diagnostic methods. The preparation for the MALDI process and the laser desorption itself also take place on this end surface; see the description further below regarding this.

A special design of these sample support pins (3) has coatings with a thin layer of α-cyano-4-hydroxycinnamic acid (HCCA). This layer is insoluble in water. If this layer is moistened with water, it adsorbs proteins, and the microbes are thus held firmly on the layer due to their coat proteins. When the moistened sample support pins (3) are pressed onto the surface of the nutrient medium, they can be shifted slightly to and fro or dabbed at slightly different locations so that the microbes from the microcolony are spread over a slightly larger surface, and thus more microbes can be picked up. The soluble proteins from the disrupted microbes are later embedded into this thin HCCA layer using methods which are as such known.

In a different design, the end surface of the sample support pins (3) is coated with an extremely thin layer of dinitrocellulose or trinitrocellulose (cellulosis dinatrate or cellulosis trinitrate). The nitrocelluloses are soluble in alcohol, acetone and other organic solvents and can thus be applied as a solution and then dried. This layer is also insoluble in water and can be moistened before it comes into contact with the surface of the nutrient medium; it then adsorbs the coat proteins of the microbes with a strong adhesive force. The nitrocelluloses do not hinder the MALDI process of the ionization of the analyte molecules.

It is also possible to apply adhesive coatings of the type used in adhesive plasters which adhere to the skin. Sample support pins with adhesive coatings can best be dabbed onto the microcolonies several times without moistening. The adhesive must be formulated so that it does not hinder the MALDI process of ionization.

In a special design of the sample support pins (3), as is shown in FIG. 1, these layers of HCCA, nitrocellulose or adhesive are applied only in central regions (1) of the end surfaces with a diameter of 0.8 millimeters, for example, while the border regions (2) of the end surfaces are coated with a hydrophobic layer. This hydrophobic border (2) simplifies the further preparation of the MALDI sample and the handling of the sample support pin. It permits, for example, easy insertion of the sample support pins into a storage container (19), where only the hydrophobic surface sits on a recess in the insertion holes in such a way that the rear ends of the sample support pins protrude from the storage container.

It is advantageous if the preparation takes place after the sample support pins (3) have been inserted into the adapter plate (10); the preparation can be done manually or in a pipetting robot. The microbes are first prepared with around 0.5 microliters of a strong acid, usually formic acid or trifluoroacetic acid (TFA), the aim being to destroy the cell walls or at least greatly weaken them. For sample support pins (3) with a hydrophobic border (2), the small drop of acid remains limited to the central hydrophilic region (1). After the acid has dried, the released proteins are then prepared with the matrix substance: with HCCA thin layers, the proteins can be embedded into the layers by a drop (around 0.5 microliters) of acetonitrile; with nitrocellulose layers, the matrix substance solution must now be added. A non-contact deposition process has proven to be successful for depositing the small quantities of liquid, where a small drop is pressed out of a central cannula in a controlled way, and a short pressure surge of gas from a second, concentric cannula releases the drop and lets it fall onto the target. It should be noted here that cell disruption and matrix addition can also be done in a single step by using a strongly acidified matrix solution.

A second embodiment of the transfer method concerns the simultaneous contact transfer of many microcolonies onto the contact surface (4) of a sample support plate (5). A sample support plate (5) with a round design is shown by way of example in FIG. 2. In principle, however, the sample support plate (5) can be any shape, with a diameter of between one and eight centimeters, which can simultaneously pick up the microbes of many microcolonies by pressing it lightly onto the surface of the nutrient medium. The contact surface (4) of the sample support plate (5) should be aligned parallel to the surface of the nutrient medium. The sample support plate (5) can be pressed on manually, but also by a device according to FIG. 5 with a robotic arm (25), for example, where the robotic arm can also control the contact pressure. The surface (4) of this sample support plate (5) can be prepared in a similar way to the sample support pins in order to bind as many microbes as possible. It can be simply moistened, for example, or can be coated with adhesive or strongly adsorptive layers.

The sample support plates (5) can also be inserted into specially shaped adapter plates (12). The adapter plates (12) have an outer contour which is necessary for introducing them into the ion source of the mass spectrometer. It is expedient if a camera now takes a digital image of the transferred microcolonies on the sample support plates. The positions of the transferred microcolonies can be determined from this image. The image can be taken after the sample support plates have been inserted into the adapter plate, because then the positions relative to the adapter plate can easily be determined. The positional data can later serve to control the spectrum acquisition.

The microbes from the individual microcolonies can be prepared in the way described above for the sample support pins; it is, however, more favorable to use a method which was similarly developed for the preparation of thin tissue sections for imaging mass spectrometry. Here it is usual to use spray mists in order to achieve a uniform preparation without strong lateral smearing of the proteins. Preparation methods of this type are described in the document DE 10 2006 059 695 B3 (M. Schürenberg, identical with GB 2 446 251 A and US 2008/0142703 A1). It should, however, be noted that the microbes on the contact surfaces have to be cell disrupted, thus destroying the relatively robust cell walls, a process which is not necessary with the preparation of thin tissue sections because the cells here are already cut open, on the one hand, and are surrounded only by thin membranes instead of robust cell walls, on the other hand.

The spectrum acquisition from the sample support plates can consist in scanning the whole contact surface, although this is usually too time-consuming. It is therefore better to use the positional data from the digital images and include only the identified positions of the microcolonies and their immediate surroundings in the spectrum acquisition.

A special embodiment of the spectrum acquisition on sample support plates can consist in acquiring the mass spectra only along the track (31) of the sample for analysis which has been plated onto the surface of the nutrient medium in a Petri dish (30) (FIG. 6). To this end it is necessary to take a photographic image of the plating of the sample for analysis onto the surface of the nutrient medium (inoculation process), for example with the aid of a long exposure or a video camera. Using this method it is also possible to analyze microcolonies which cannot be identified photographically, without carrying out mass spectrometric analyses on the whole contact surface.

Examples for the two preferred methods shall now be described in slightly more detail: the first method using HCCA-coated sample support pins (3), and the second method using larger sample support plates (5).

For the first method, the microbes are cultured into microcolonies in Petri dishes, on surfaces which contain nutrient media, in around eight hours. The surfaces containing the nutrient media can be agar surfaces, but also microporous membranes with nutrient solutions, from which it is easier to lift off the microbes, for example a membrane made of silicone rubber with pores less than 100 nanometers in diameter. The Petri dishes (22) are then fixed on the base (20) of a device according to FIGS. 5 and 7, and the surface of the nutrient medium is photographed with a camera (24), which is permanently installed on the device. Cameras are available with high spatial resolutions of about 20 micrometer or even better for the distance between camera and Petri dish in FIG. 7. As outlined above, identifiable microcolonies should have diameters of 50 to 200 micrometers. If higher spatial resolution is required, the camera can acquire several pictures of parts of the agar surface each by moving the Petri dish. The image of the surface is shown on a monitor, and the user can now select a preselected number of microcolonies by clicking on them. The number of microcolonies to be selected depends on the analytical task, and especially on whether it is expected that the sample supplied for analysis contains only a single species of microbe or several different species. If different types of colony can be seen, each type of colony can be included in the selection.

The device also contains a controllable robotic arm (25, 26, 27), which can pick up the sample support pins (3) from a storage container (not shown in FIG. 5, 19 in FIG. 7) and press them onto the surface of the nutrient medium in the Petri dish (22) with high positional accuracy. The end surfaces of the sample support pins (3) preferably have a diameter of around two millimeters and, as is shown in FIG. 1, are coated in a central region (1), measuring around 0.8 millimeters in diameter, with a thin layer of α-cyano-4-hydroxycinnamic acid (HCCA); the surrounding border (2), which is around 0.6 millimeters wide, has a hydrophobic coating. The robotic arm (27) first presses the end surface of the sample support pin (3) onto a moist sponge in order to moisten the hydrophilic part of the surface. The robotic arm presses the end surface very gently onto the center of one of the selected microcolonies which are moved by moving support (28) into the right position, controlled by the positional data for this microcolony. If the sample support pin (3) is made of metal, it is usually sufficient to release the sample support pin above the surface so that it comes to rest on the surface under its own weight. Moving the sample support pin to and fro slightly by a few tenths of a millimeter in different directions, or repeated dabbing, helps to distribute the microbes over a slightly larger area than corresponds to the diameter of the colony. The adsorptive force of the thin layer coating means that a large fraction of all the microbes in the microcolony can be picked up, especially if the nutrient medium is in a material from which the microbes can be lifted off particularly easily. If the adsorptive area (1) of 0.8 millimeters diameter is densely coated with bacteria of average size (around 1×2 micrometers), it can pick up a quarter of a million bacteria, so it is certainly large enough to pick up the microbes from microcolonies. Initial experience has shown that if the microcolony contains only around 1000 microbes, almost all of them can be transferred onto the contact surface.

The sample support pin (3) can then for example be gripped by a second robotic arm (not shown in FIG. 5) in order to turn it round and insert it into a closely fitting hole in an adapter plate (10). However, the sample support pins may also be at first placed back at free positions in the delivering plate (19). After all sample support pins have been coated with bacteria from microcolonies, the pins are transferred to the adapter plate (10). The adapter plate (10) has a shape which allows it to be inserted, with all pin-like sample supports, into the mass spectrometer used. The end surfaces of the sample support pins (3) should be exactly flush with the surface of the adapter plate (10) in order to later provide a plain and uninterrupted surface for the formation of homogeneous acceleration fields for the ions in a time-of-flight mass spectrometer. An adapter plate (10) having the shape and size of a microtiter plate can hold 8×12=96 sample support pins (3), for example; a denser packing of up to 384 sample support pins is possible, but not necessarily expedient. The time required for the contact transfer of 96 microcolonies depends largely on the number of cultured Petri dishes which need to be photographed and evaluated; in general, this work can be accomplished in around a quarter of an hour. Once the adapter plate (10) has been filled with a sufficient number of sample support pins (3), preparation of the samples can start. The preparation can be carried out particularly well in a pipetting robot, which releases the drops without contact.

The microbes must first be prepared for cell disruption by weakening or destroying their strong cell walls. As usual, this can be done by acids such as formic acid or trifluoroacetic acid. To this end, only around 0.5 microliters of solution must be applied to the hydrophilic central regions (1) of each sample support pin (3). The droplets are held there and cannot flow into the surrounding hydrophobic border regions (2). After only a few minutes, the cell walls are sufficiently weakened and the acids can be dried, by introducing the adapter plate (10) into an evacuable desiccator, for example. Then around 0.5 microliters of an acetonitrile/water mixture is added, which penetrates into the cells and makes them burst so that the soluble proteins from the inside are released. At the same time, the acetonitrile slightly dissolves the topmost part of the HCCA thin layer. The evaporation of the acetonitrile causes recrystallization to occur, whereby most of the protein molecules held on the crystal surfaces by adsorption are incorporated into the crystal lattice.

The sensitivity of the MALDI process of ionization can also be increased by the removal of salt ions such as $Na^+$ or $K^+$, which are known to suppress the ionization. This can for example be achieved by adding ammonium citrate or ammonium tartrate to the matrix solution, or by using salt-tolerant matrix substances such as 3,4-diaminobenzophenone (DABP). Simple washing is also effective; applying 0.5 microliters of deionized water and removing it again by suction eliminates most of the salts and other substances which could hinder the MALDI process of ionization.

It is particularly favorable if all liquids are deposited without contact in the form of small droplets because then it is not necessary to use new pipette tips every time. Contact-free deposition has proven to be successful for depositing the small quantities of liquid below one microliter, where a tiny drop is pressed out of a microcannula in a controlled way. The drop is released from the central microcannula by a short pressure surge of gas from a second, concentric cannula and falls vertically onto the target. To remove the washing water from all the sample support pins simultaneously, a sheet of blotting paper can be placed on the adapter plate and immediately removed again.

The preparation for 96 samples can be carried out in less than ten minutes. The adapter plate (10) with the fully prepared MALDI samples can then be introduced via a vacuum lock into the ion source of a mass spectrometer. The acquisition of mass spectra, each composed of hundreds of individual spectra, requires only around one second per sample in modern mass spectrometers. If the identification program can operate quickly enough, the identification results for 96 MALDI samples can be available less than five minutes after the introduction of the adapter plates. The total time required for the work after the completion of culturing, i.e., contact transfer, sample preparation and spectrum acquisition, therefore amounts to around half an hour.

The second example which is to be explained here concerns the simultaneous removal of the microbes from several microcolonies with a larger sample support plate (5) and the type of preparation of the microbes on the contact surface.

After the microbes have been cultured in a Petri dish and a photograph taken of the microcolonies on the Petri dish, a sample support plate (5) is pressed onto the surface of the nutrient medium by a device such as the one shown in FIG. 5. The sample support plate (5) in this example is round with a diameter of 2.5 centimeters, and shall be coated with a thin layer of a nitrocellulose in order to make it strongly adsorptive for the coat proteins of the microbes. The device can press the sample support plate (5) with an adjustable contact pressure onto a region of the surface of the nutrient medium selected by the user in advance. The sample support plate (5) here can be moved to and fro by a few tenths of a millimeter in order to distribute the microbes over a slightly larger area.

After it has been taken off the surface of the nutrient medium, the sample support plate (5) can be inserted, along with further sample support plates (5), into the surface of an adapter plate (12) so as to be flush. The adapter plate (12) has a shape which enables it to be introduced into the mass spectrometer used. A high-resolution digital image is taken of the adapter plate (12) with the inserted sample support plates (5), using suitable lighting. This image indicates the transferred microbe colonies and serves to determine their positions relative to positional markers of the adapter plates. If the contact surface of the sample support plates is highly polished, and the lighting is incident obliquely onto this surface, the microbes can be identified with high sensitivity by their scattered light on a dark background. The adapter plate can now be prepared for the ionization by matrix-assisted laser desorption. This can be done using simple spray guns to generate fine aerosols or preferably in a spray apparatus developed especially for this purpose ("ImagePrep", Bruker Daltonik GmbH, Bremen/Germany). The spray apparatus converts a liquid into a mist, whose microdroplets deposit uniformly on the surface. The density of the deposited droplets can be controlled in order to largely prevent any lateral running Spraying and drying periods may alternate in a controlled way, as is known from the preparation of thin tissue sections.

The robust cell walls of the microbes must first be weakened by spraying on formic acid or trifluoroacetic acid. A solution of the matrix substance is then sprayed on, thereby completely destroying the cell walls and releasing the soluble proteins from the interior of the cells. Alternating periods of spraying and drying now cause microcrystals to grow, with increasing embedding of the soluble proteins from the microbe cells. The procedure is terminated when the microcrystalline layer has reached a thickness of around two to three micrometers. If the matrix material is water-insoluble, the microcrystalline surface can now simply be rinsed with pure water in order to remove all salts and other harmful, but water-soluble, substances. In order to produce a largely continuous microcrystalline layer, a suspension of extremely fine solid crystallization nuclei can be applied by nebulization and dried before the matrix solution is sprayed on. The crystallization nuclei can be composed of extremely finely ground quartz sand, for example; the crystallization nuclei ensure the matrix material crystallizes over the whole surface.

The adapter plate (12) is introduced into a mass spectrometer. The ion source of the mass spectrometer contains devices with which the adapter plate can be moved in two directions with positional accuracies of a few micrometers. By linking with the positional data of the microcolonies in the digital image, the microbe positions of these colonies on the sample support plate can now be individually selected and analyzed. All identifiable microcolonies can be analyzed, or only the automatically selected microcolonies, or the colonies which the user has selected visually in advance. The microbe identifications originating from the mass spectra can then be assigned again to the microcolonies on the digital image: clicking on a microcolony on the monitor can then display the name of the species. Particularly when the analyzed samples are diagnostic samples, it is also possible to output the results in the form of tables for passing on to the physician who took the samples and sent it to the mass spectrometric laboratory for analysis.

With this method it is not possible to exclude the possibility that some microcolonies are not identified on the digital image because they are too small or because there is no color contrast between them and the surface of the sample support even under adapted lighting conditions. If this danger exists, a special method can be used whereby the track (31) of the sample applied to the surface of the nutrient medium is scanned analytically with the laser shots of the MALDI method. This requires that the plating (inoculation) of the sample for analysis is recorded and documented, for example by a fixed camera with long exposure, or by a video camera. Usually, the sample for analysis is manually plated in the form of a zigzag line with a few movements to and fro, as is depicted schematically as a track (31) in FIG. 6. Once this track has been documented, the adapter plate in the mass spectrometer can be moved in such a way that the track of the plating can be analytically sampled in a series of spectrum acquisitions. This makes it possible to also include any microcolonies which have remained invisible although they have formed sufficient number of microbes.

The two methods of transfer and preparation described above can be modified or extended in many different ways. In particular, it is possible to continue to culture the remaining microbes in the Petri dishes, after the microbes have been removed with the aid of sample support pins or sample support plates, in order to also discover and identify more slowly growing microbes, albeit after a longer culture period. It may be expedient to destroy the microcolonies of fast-growing microbes or to remove them mechanically. Here too, the digital images taken after a short culture period are helpful in order to discover further colonies after a longer cultivation. These can then be removed with sample support pins or sample support plates and analyzed for identification, just like the original microcolonies which have been identified in the first sampling.

If it is suspected that particularly slow-growing but dangerous microbes are present, the Petri dishes with the nutrient media can be repeatedly examined at suitable intervals, every eight hours, for example, for the growth of microcolonies, in a special embodiment of the method. If fast-growing microbes which are not of interest here are present and cause interference, the microcolonies of these microbes can be destroyed in these analytical cycles, or be completely removed, after contact removal with sample support pins where necessary. This reduces the danger that the fast-growing microbes will overgrow the slow-growing ones. The slow-growing microbes can be identified using specified features, such as their slow growth, but also other features such as the shape and color of the colonies, and are then removed from the surface of the nutrient medium by contact transfer onto sample support pins and fed to the analysis.

Devices other than those shown in FIG. 5 can also be used for the contact transfer. For example, it is possible to lower sample support plates or sample support pins onto the surface of the nutrient medium not with a complicated robotic arm, but simply with a device which can only be moved vertically, such as a piezo-controlled linear motor or small bellows. The length and contact pressure of the bellows can be controlled by a small pump. FIG. 7 illustrates such a device with a small linear motor (27) for lowering a sample support pin. In order to reach every position on the surface of the nutrient medium, the dish (22) with the nutrient medium can be placed on a movement device (28) which can move the dish horizontally in two directions. Such a device supports automation.

The device (27) for the vertical motion of the sample support plates or sample support pins can preferably be rotated between two angular positions about a joint (26) on the support column in order to keep the line of sight of the camera unobstructed, on the one hand, and to pick up the sample support plates or sample support pins from storage containers (19), on the other hand. These storage containers (19) can also be on a horizontally movable table (29). FIG. 7 depicts a storage container (19) with 4×6=24 sample support pins by way of example. The sample support pins can be returned to the storage container after being coated with microbes. In the storage container, only the hydrophobic border (2) of their end surface sits on a recess of the insertion hole. Since this border is not coated with microbes, there is no loss of microbes.

As already stated above, many other types of ionization of substances which are located in a layer on a sample support can be used instead of MALDI ionization, such as cluster bombardment ionization in accordance with EP 1 200 984 B1, Desorption Electrospray Ionization (DESI) in accordance with WO 2005/094389 A2 or Matrix Assisted Laser Desorption Electrospray Ionization (MALDESI) in accordance with DE 10 2004 002 729 B2. Except for MALDESI, the preparation of a mass spectrometric sample then consists essentially in the cell disruption of the microbes on the sample support.

The invention claimed is:

1. A method for the mass spectrometric analysis of microbes on the surface of a nutrient medium in a mass spectrometer with ionization by matrix-assisted laser desorption, comprising the steps:
   (a) microbes are transferred by direct contact onto a contact surface of a sample support,
   (b) the transferred microbes are cell disrupted on the contact surface of the sample support and the molecular constituents of the microbes are prepared as a MALDI sample, and (c) the sample support with the MALDI sample is transferred to the mass spectrometer for analysis.

2. A method according to claim 1, wherein the end surface of a pin-shaped sample support is brought into contact with microbes, the contact surface of the pin-shaped sample support being so small that only microbes of an individual colony are transferred onto the pin-shaped sample support.

3. Method according to claim 2, wherein, after the microbes have been transferred, the pin-shaped sample support is inserted into an adapter plate in such a way that the end surface of the pin-shaped sample support is essentially flush with the surface of the adapter plate.

4. A method according to claim 3, with the steps:
acquiring an image of the surface of the nutrient medium,
determining the positions of colonies from the image,
performing contact transfer of microbes at the determined positions onto a pin-shaped sample support in each case,
inserting the pin-shaped sample supports into an adapter plate,
preparing MALDI samples from the microbes on the pin-shaped sample supports,
introducing the adapter plate into a mass spectrometer, and
acquiring spectra with ionization by matrix-assisted laser desorption at the positions of the pin-shaped sample supports in the adapter plate.

5. A method according to claim 2, wherein the end surfaces of the pin-shaped sample supports have surfaces of less than nine square millimeters.

6. A method according to claim 1, wherein a plate-shaped sample support is brought into contact with microbes, and the contact surface of the plate-shaped sample support is so large that microbes from several colonies are transferred simultaneously onto the plate-shaped sample support.

7. A method according to claim 6, wherein an image is acquired of the contact surface after the microbes have been transferred onto the plate-shaped sample support, and the positions of the transferred microbes on the plate-shaped sample support are determined from the image.

8. A method according to claim 7, wherein, after the imaging, the MALDI samples are prepared only at the determined positions and the mass spectrometric analyses are carried out only on the prepared MALDI samples.

9. A method according to claim 7, wherein, after the imaging, a matrix solution is applied to the whole contact area of the sample support and the mass spectrometric analyses are carried out only at the determined positions.

10. A method according to claim 6, wherein, during inoculation of the sample for analysis onto the surface of the nutrient medium, the track of the inoculation is recorded and the mass spectrometric analysis is carried out only along the recorded track.

11. A method according to claim 1, wherein the microbes on the sample support are cell disrupted by adding a suitably aggressive matrix solution.

12. A method according to claim 1, wherein the microbes are cultured on the surface of the nutrient medium for less than eight hours before being transferred onto the sample support.

13. A method according to claim 1, wherein the surface of the nutrient medium is examined repeatedly for the growth of microbe colonies during the culture process, and contact transfer takes place when colonies are detected.

14. A method according to claim 1, wherein the contact surface of the sample support is prepared with protein-adsorptive or adhesive regions.

15. A method for the mass spectrometric analysis of microbes on the surface of a nutrient medium in a mass spectrometer, comprising the steps:
(a) microbes are transferred onto a contact surface of a sample support by direct contact,
(b) the transferred microbes are cell disrupted on the contact surface of the sample support, and
(c) the sample support with the molecular constituents of the disrupted microbes are introduced into the mass spectrometer for analysis.

16. A method for the identification of microbes grown on the surface of a nutrient medium by comparing mass spectra of their molecular constituents with reference mass spectra, comprising the steps:
(a) transferring microbes by direct contact of a sample support contact surface with one or more colonies on the nutrient medium,
(b) cell disrupting the transferred microbes and preparing their molecular constituents for the acquisition of mass spectra on the sample support contact surface, and
(c) introducing the sample support with the prepared samples into a mass spectrometer, and
(d) acquiring mass spectra of the molecular constituents of the microbes for their identification.

* * * * *